United States Patent [19]

Miyamoto et al.

[11] Patent Number: 5,214,174
[45] Date of Patent: May 25, 1993

[54] PLATINUM COMPLEX AND ANTI-TUMOR AGENT COMPRISING SAID COMPLEX AS ACTIVE INGREDIENT

[75] Inventors: Ken Miyamoto, Tokyo; Yuichi Fujii; Toshiaki Fujihashi, both of Inashiki, all of Japan

[73] Assignee: Tsumura & Co., Tokyo, Japan

[21] Appl. No.: 752,462

[22] PCT Filed: Dec. 14, 1990

[86] PCT No.: PCT/JP90/01638

§ 371 Date: Oct. 15, 1991

§ 102(e) Date: Oct. 15, 1991

[87] PCT Pub. No.: WO91/09042

PCT Pub. Date: Jun. 27, 1991

[30] Foreign Application Priority Data

Dec. 15, 1989 [JP] Japan ............................. 1-323874

[51] Int. Cl.⁵ ............................................. C07F 15/00
[52] U.S. Cl. ............................................. 556/137
[58] Field of Search ........................ 556/137; 514/492

[56] References Cited

U.S. PATENT DOCUMENTS

| | | | |
|---|---|---|---|
| 4,169,846 | 10/1979 | Kindani et al. ................ | 260/429 R |
| 4,359,425 | 11/1982 | Totani et al. ................... | 556/137 |
| 4,739,087 | 4/1988 | Speer et al. .................... | 556/137 |
| 4,921,984 | 5/1990 | Nowatari et al. ............... | 556/137 X |

FOREIGN PATENT DOCUMENTS 62-289591 12/1987 Japan.
1-156990 6/1989 Japan.

OTHER PUBLICATIONS

Pasini et al, "New Cisplatin Analogues . . .", *Angewandte Chemie*, International Ed. English, vol. 26, No. 7, Jul. 1987, pp. 615–624.
Chemical Abstracts, vol. 87, 1977, p. 11, abstract No. 87:15694z, Hall et al, "Analogs of sulfato 1,2-diaminocyclohexane platinum (II) (SHP)".
Chemical Abstracts, vol. 94, 1981, p. 42, abstract No. 94:167604c, Speer et al, "Preclinical evaluation of some cisplatin analogs as potential antitumor agents".

*Primary Examiner*—Arthur C. Prescott
*Attorney, Agent, or Firm*—Burns, Doane, Swecker & Mathis

[57] ABSTRACT

Disclosed are a novel platinum complex represented by the following formula I or a steric isomer thereof, an anti-tumor agent comprising this complex as the effective ingredient, and a method of curing a tumor by using this complex:

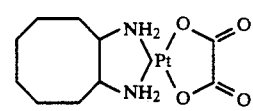

I

This complex is advantageous in that the toxicity is low and the anti-tumor activity is high.

3 Claims, No Drawings

PLATINUM COMPLEX AND ANTI-TUMOR AGENT COMPRISING SAID COMPLEX AS ACTIVE INGREDIENT

TECHNICAL FIELD

The present invention relates to a novel platinum complex having an anti-tumor activity and which is valuable as a medicine such as an anti-tumor agent.

BACKGROUND ART

Some platinum complexes represented by cisplatin have a remarkable anti-tumor effect, and cisplatin has been applied to various cases. Nevertheless, the toxicity, such as the kidney toxicity, of cysplatin is very strong, and this strong toxicity is an obstacle to a medical treatment. Accordingly, the development of a medicine having a toxicity lower than those of conventional platinum complexes, and a higher anti-tumor effect, is required.

DISCLOSURE OF THE INVENTION

With a view to solving this problem, the present inventors synthesized various platinum complexes and examined the anti-tumor effects thereof, and as the result, the inventors found a platinum complex having a toxicity lower than those of the conventional platinum complexes, and a higher anti-tumor activity, and the present invention was completed based on this finding.

More specifically, in accordance with the present invention, there are provided a novel platinum complex represented by the following formula I or a steric isomer thereof (hereinafter referred to as "the compound of the present invention"):

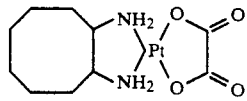

I and an anti-tumor agent comprising this complex as an active ingredient.

Furthermore, there is provided a method of remedying a tumor with the compound of the present invention.

BEST MODE OF CARRYING OUT THE INVENTION

The steric isomer of the compound of the formula I includes compounds represented by the following formulae

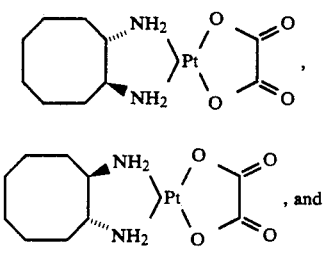

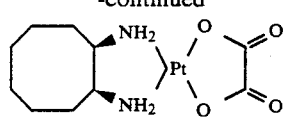

The compound of the present invention can be prepared, for example, according to the following procedures.

A dinitrato platinum complex having 1,2-cyclooctanediamine as a carrier ligand is used as the starting material, and this complex is brought into contact with an $OH^-$ anion exchange resin, to convert the nitro group of the complex to a hydroxyl group. The intended complex is obtained by reacting the above complex with oxalic acid, and recrystallization can be carried out by using an appropriate solvent such as water, according to need.

Furthermore, after the termination of the reaction, a filtration can be carried out by using an adsorbent such as active carbon, according to need, whereby a more refined crystal can be obtained.

As a specific example of the dinitrato platinum complex, there can be mentioned dinitrato(diaminocyclooctane)platinum (II).

As the dinitrato(diaminocyclooctane)platinum (II), there are known dinitrato-(1R,2R)-diaminocyclooctane platinum (II) and dinitrato-(1S,2S)-diaminocyclooctane platinum (II) as the trans-form, and dinitrato-cis-diaminocyclooctane platinum (II) as the cis-form. The present invention includes all of the corresponding isomers prepared from these starting materials and mixtures comprising these isomers at optional ratios.

As a specific example of the $OH^-$ type anion exchange resin, there can be mentioned Diaion SA1-0AOH (supplied by Mitsubishi Kasei).

As the contact method, any method whereby the platinum complex is brought into contact with the resin, for example, the batch methods and column methods, can be adopted, but in view of the operation efficiency, a column method is preferably adopted.

For the reaction with oxalic acid, there is preferably adopted a method in which oxalic acid dihydrate is dissolved in an amount slightly smaller than the chemical equivalent to the starting platinum complex, and the solution is allowed to stand for about 12 to about 36 hours. After termination of the reaction, the aqueous solution is concentrated or a precipitation is effected by addition of a solvent such as methanol, and the precipitated crystal is recovered by filtration and dried to obtain the intended complex.

The structure of the compound of the present invention has been confirmed by elementary analysis, infrared absorption spectrum analysis and the like.

The anti-tumor effect of the compound of the present invention will now be described with reference to the following experiments.

Experiment 1

L1210 mouse leukemia cells, P388 mouse leukemia cells, Hela human uterine neck cancer cells, T24 human bladder cancer cells or MCF7 human mammary cancer cells were suspended in Eagle medium (Hela and T24) containing 10% bovine fetal serum, PRM11640 medium (L1210 and MCF7) or PRM11740 medium (P388) mixed with $5 \times 10^{-5}M$ mercaptoethanol, and the cells were seeded on a 96-well plate at an inoculum size of $3 \times 10^3$ cells per hole. A compound obtained in an example described below or cysplatin (CDDP) was diluted with physiological saline solution and added to the medium at various concentrations. Culturing was conducted at 37° C. for 48 hours in a carbon dioxide incubator, and the propagation of cells was determined by the MTT [3-(4,5-dimethylthiazol-2-yl-)-2,5-diphenyl tetrazolium bromide] method (J. Immunol. Method, 65, 55, 1983). The absorbance A after 48 hours of culturing at each concentration, the absorbance B after 48 hours of culturing in the control, and the absorbance C before addition of the compound obtained in the example were determined, and the propagation reaction rate D of each concentration was calculated from the following formula:

$$D = \frac{A - C}{B - C} \times 100$$

The concentration IC$_{50}$, unit: μg/ml) of the compound obtained in the example giving the value corresponding to 50% of the value of the control was determined from the curve showing the relationship between the concentration of the compound obtained in the example and the propagation reaction rate.

The results are shown in Table 1.

TABLE 1

Inhibition of Propagation of Mouse and Human Cancer Cells

| Cell Name | IC$_{50}$ (μg/ml) | |
|---|---|---|
| | CDDP | Compound Obtained in Example 1 |
| L1210 | 0.46 | 0.03 |
| P388 | 0.09 | 0.06 |
| P388 | 0.09 | 0.06 |
| HeLa | 1.42 | 0.29 |
| T24 | 1.51 | 1.43 |
| MCF7 | 3.28 | 0.41 |

Experiment 2

Mouse leukemia L1210 cells ($1 \times 10^5$) were transplanted into the abdominal cavity of a 6-weeks-old female BDF$_1$ mouse. Then, continuously for 3 days from the next day, a compound of a compound obtained in an example described below or CDDP was administered to the abdominal cavity once a day. In the control group, physiological saline solution alone was similarly administered.

The anti-tumor effect was evaluated based on the life prolongation ratio (T/C value) determined from the average survival day numbers of the group of the compound obtained in the example and the control group after 30 days from the transplantation of L1210. On the 30th day from the transplantation, the experiment was concluded. In the case of mice surviving for more than 30 days, the survival day number was regarded as 30.

$$T/C(\%) = \frac{\text{average survival day number in compound-administered group}}{\text{average survival day number in control group}} \times 100$$

The average survival day number at each dose, the T/C value (%) and the ratio of the number of surviving mice upon termination of the experiment to the number of tested mice are shown in Table 2. The ILS$_{30}$ value (the dose giving a 30% life-prolonging effect over the control group), the ILS$_{max}$ value (the dose giving a highest life-prolonging effect), the TR value (cure ratio; ILS$_{max}$/ILS$_{30}$) and the CR value (the ratio of the number of mice completely cured at the ILS$_{max}$ value and the number of mice showing no propagation of a tumor after 30 days from the transplantation to the number of tested mice) are shown in Table 3.

Note, ① indicates the ratio of the number of surviving mice to the number of tested mice.

TABLE 2

| | Dose (mg/kg) | Average Survival Day Number | T/C (%) | ① |
|---|---|---|---|---|
| Compound Obtained in Example 1 | 0.3 | >16.8 | >183 | 1/6 |
| Compound Obtained in Example 1 | 1.0 | >19.7 | >214 | 1/6 |
| Compound Obtained in Example 1 | 3.0 | >20.3 | >220 | 2/6 |
| Compound Obtained in Example 1 | 10.0 | >30.0 | >326 | 6/6 |

TABLE 3

| | ILS$_{30}$ (mg/kg) | ILS$_{max}$ (mg/kg) | TR | CR |
|---|---|---|---|---|
| Compound Obtained in Example 1 | 0.06 | 10.0 | 167 | 6/6 |
| CDDP | 1.5 | 6.0 | 4 | 3/6 |

From the foregoing results, it has been confirmed that the compound of the present invention has an excellent anti-tumor activity.

When the acute toxicity test of the compound of the present invention was carried out by using male mice of the ICR family, it was found that LD$_{50}$ of the compound of the present invention was 29.5 mg/kg in the case of an administration into the abdominal cavity, and since this LD$_{50}$ value of CDDP is 14.6 mg/kg, it is understood that the compound of the present invention is safe.

Namely, it is considered that the compound of the present invention has an excellent anti-tumor activity and is valuable as an anti-tumor agent having a low toxicity.

The doses and preparations of the compound of the present invention will now be described.

The compound of the present invention can be administered to humans and animals directly or together with a conventional drug carrier. The administration mode is not particularly critical, and an appropriate administration mode is selected according to need. For example, there can be mentioned an agent for oral administration, such as a tablet, a capsule, a granule, a fine particle or a powder, and an agent for non-oral administration, such as an injection or a suppository.

In order for the compound of the present invention to attain the intended effect as an agent for oral administration, it is considered preferable to administer 10 mg to 1 g of the compound of the present invention to an adult per day dividedly in several times, though an appropriate dose is changed according to the age, body weight and disease state of a patient.

The agent for oral administration can be prepared according to customary procedures by using, for example, starch, lactose, refined sugar, mannitol, carboxymethyl cellulose, corn starch and inorganic salts.

The preparation of this type can further comprise a binder, a disintegrating agent, a surface active agent, a lubricant, a flowability improver, a taste improver, a coloring agent, a perfume and the like. Specific examples of these additives are described below.

(Binder)

Starch, dextrin, gum arabic powder, gelatin, hydroxypropyl starch, methyl cellulose, sodium carboxymethyl cellulose, hydroxypropyl cellulose, crystalline cellulose, ethyl cellulose, polyvinyl pyrrolidone and macrogol.

(Disintegrating Agent)

Starch, hydroxypropyl starch, sodium carboxymethyl cellulose, calcium carboxymethyl cellulose, carboxymethyl cellulose and lowly substituted hydroxypropyl cellulose.

(Surface Active Agent)

Sodium lauryl sulfate, soybean lecithin, sucrose fatty acid ester and polysorbate 80.

(Lubricant)

Talc, waxes, hydrogenated vegetable oil, sucrose fatty acid ester, magnesium stearate, calcium stearate, aluminum stearate and polyethylene glycol.

(Flowability Improver)

Soft silicic anhydride, dry aluminum hydroxide gel, synthetic aluminum silicate and magnesium silicate.

The compound of the present invention can be administered in the form of a suspension, emulsion, syrup or elixir. The preparation of this type can further comprise a taste improver, an odor improver and a coloring agent.

In order for the compound of the present invention to exert the intended effect as the agent for non-oral administration, it is considered preferable to administer the compound of the present invention in an amount of 5 to 600 mg per day to an adult by intravenous injection, instillation, hypodermic injection or intramuscular injection, though the amount administered is changed according to the age, body weight and disease degree of a patient.

The agent for non-oral administration can be prepared according to known procedures, and as the diluent, there can be used distilled water for injection, physiological saline solution, an aqueous solution of glucose, a vegetable oil for injection, sesame oil, peanut oil, soybean oil, corn oil, propylene glycol and polyethylene glycol. A fungicide, an antiseptic agent and a stabilizer can be added according to need. In view of the stability of the agent for non-oral administration, a method can be adopted in which the agent is filled in a vial or the like, water is removed by a usual freeze-drying technique and a liquid agent is prepared again just before the administration. Appropriate additives such as an isotonic agent, a stabilizer, an antiseptic agent and a lenitive agent can be added according to need.

As the other agent for non-oral administration, there can be mentioned coating agents such as a lotion for external application and an ointment, and a suppository for intrarectal application, and these can be prepared according to customary procedures.

The present invention will now be described in detail with reference to the following examples, that by no means limit the scope of the invention.

EXAMPLE 1

Dinitro-trans-cyclooctanediamine-platinum as the starting material was synthesized by using transcyclooctanediamine containing optical isomers having (1R,2R) and (1S,2S) arrangements at a ratio of 1:1 as the carrier ligand. Then, 12.4 g of this trans-compound was dissolved in 400 ml of distilled water, and the solution was passed through a column filled with 300 ml of Diaion SA10AOH and fluxed with distilled water. Then, 3.3 g of oxalic acid was dissolved in the effluent and reaction was carried out at 30° C. for 12 hours. After termination of the reaction, the reaction liquid was passed through a column filled with active carbon as the adsorbent and fluxed with distilled water. The effluent was concentrated, and recrystallization was carried out by using water to obtain 8.5 g of a light yellow crystal.

By the following physical and chemical properties, this yellow crystal was identified as a 1:1 mixture of oxalate-(1R,2R)-diaminocyclooctane platinum (II) and oxalate-(1S,2S)-diaminocyclooctane platinum (II), included in the scope of the compound of the present invention.

Elementary Analysis Values (as $C_{10}H_{18}O_4N_2Pt$)
Calculated values (%): C=28.23, H=4.27, N=6.59
Measured values (%): C=28.26, H=4.25, N=6.65
Infrared Absorption Spectrum $\nu_{max}^{KBr}cm^{-1}$ 3450, 3050, 1710, 1390, 815

EXAMPLE 2

In methanol was dissolved 10 mg of the compound obtained in Example 1, and the solution was subjected to optical resolution by column chromatography using a separating optical resolution column [Ultron ES-OVM (20 mm in diameter and 25 cm in length; particle size of 10 μm; supplied by Shinwa Kako).

The column conditions were such that the moving phase comprised 100 mM sodium perchlorate (0.2% $H_3PO_4$) and acetonitrile at a ratio of 90:10, the flow rate was 0.5 ml/min, the column temperature was maintained at a constant level of about 25° C., and detection was carried out by RI (RANGE ½). The fraction A flowing out in the vicinity of 4 minutes and 30 seconds and the fraction B flowing out in the vicinity of 6 minutes and 30 seconds were collected. Each fraction was subjected to a desalting operation and the solvent was removed by distillation, whereby 4.5 mg of (−)-oxalate diaminocyclooctane platinum (II) having a specific rotation described below and 5.0 mg of (+)-oxalate diaminocyclooctane platinum (II) having a specific rotation described below were obtained.
Specific Rotations
Fraction A: $[\alpha]_D^{20} = -55°$ (C=0.1, MeOH), Fraction B: $[\alpha]_D^{20} = +46°$ (C=0.1, MeOH)

EXAMPLE 3

| | |
|---|---|
| (1) Corn starch | 52 g |
| (2) Crystalline cellulose | 40 g |
| (3) Calcium carboxymethyl cellulose | 5 g |
| (4) Light silicic anhydride | 0.5 g |
| (5) Magnesium stearate | 0.5 g |
| (6) Compound obtained in Example 1 | 2 g |
| Total | 100 g |

According to the above-mentioned recipe, components (1) through (6) were homogeneously mixed, and the mixture was compression-molded by a tableting machine to obtain tablets, each having a weight of 200 mg.

Each tablet contained 4 mg of the compound obtained in Example 1. Three to 50 tablets were administered to an adult per day, dividedly several times.

EXAMPLE 4

| (1) Crystalline cellulose | 92.5 g |
|---|---|
| (2) Magnesium stearate | 0.5 g |
| (3) Calcium carboxymethyl cellulose | 5 g |
| (4) Compound obtained in Example 1 | 2 g |
| Total | 100 g |

According to the above-mentioned recipe, components (1) and (4) and a part of component (2) were homogeneously mixed, the mixture was compression-molded and the molded product was pulverized. Component (3) and the remainder of component (2) were mixed with the pulverized product, and the mixture was compression-molded by a tableting machine to obtain tablets, each having a weight of 200 mg. Each tablet contained 4 mg of the compound obtained in Example 1. Three to 50 tablets were administered to an adult per day, dividedly several times.

EXAMPLE 5

| (1) Crystalline cellulose | 42.5 g |
|---|---|
| (2) 10% Solution of hydroxpropyl cellulose in ethanol | 50 g |
| (3) Calcium carboxymethyl cellulose | 5 g |
| (4) Magnesium stearate | 0.5 g |
| (5) Compound obtained in Example 1 | 2 g |
| Total | 100 g |

According to the above-mentioned recipe, components (1), (2) and (5) were homogeneously mixed and kneaded according to customary procedures, and the mixture was granulated by an extrusion granulator and the granulation product was dried and disintegrated. Then, the disintegration product was mixed with components (3) and (4) and the mixture was compression-molded by a tableting machine to obtain tablets, each having a weight of 200 mg.

Each tablet contained 4 mg of the compound obtained in Example 1. Three to 50 tablets were administered to an adult per day, dividedly several times.

EXAMPLE 6

| (1) Corn starch | 93 g |
|---|---|
| (2) Magnesium stearate | 0.5 g |
| (3) Calcium carboxymethyl cellulose | 5 g |
| (4) Light silicic anhydride | 0.5 g |
| (5) Compound obtained in Example 1 | 1 g |
| Total | 100 g |

According to the above-mentioned recipe, components (1) through (5) were homogeneously mixed, compression-molded by a compression molding machine, pulverized by a pulverizing machine and sieved to obtain a granule.

In 1 g of this granule was contained 10 mg of the compound obtained in Example 1, and 1 to 20 g of the granule was administered to an adult per day, dividedly several times.

EXAMPLE 7

| (1) Crystalline cellulose | 69 g |
|---|---|
| (2) 10% Solution of hydroxypropyl cellulose in ethanol | 30 g |
| (3) Compound obtained in Example 1 | 1 g |
| Total | 100 g |

According to the above-mentioned recipe, components (1) through (3) were homogeneously mixed and kneaded, granulated by an extrusion granulator, dried, and sieved to obtain a granule.

In 1 g of this granule was contained 10 mg of the compound obtained in Example 1, and 1 to 20 g of the granule was administered to an adult per day, dividedly several times.

EXAMPLE 8

| (1) Corn starch | 97.5 g |
|---|---|
| (2) Light silicic anhydride | 0.5 g |
| (3) Compound obtained in Example 1 | 2 g |
| Total | 100 g |

According to the above-mentioned recipe, components (1) through (3) were homogeneously mixed, and 200 mg of the mixture was filled in a capsule No. 2.

Each capsule contained 4 mg of the compound obtained in Example 1, and 3 to 50 capsules were administered to an adult per day, dividedly several times.

EXAMPLE 9

| (1) Distilled water for injection | appropriate amount |
|---|---|
| (2) Glucose | 200 mg |
| (3) Compound obtained in Example 1 | 100 mg |
| Total | 5 ml |

Components (2) and (3) were dissolved in distilled water for injection, and the solution was charged into an ampoule having a capacity of 5 ml and was sterilized at 121° C. for 15 minutes under pressure to obtain an injection.

INDUSTRIAL APPLICABILITY

The present invention can be effectively used in the medicinal field as a remedy for tumors.

We claim:

1. A novel platinum complex represented by the following formula I or a steric isomer thereof:

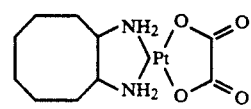

I

2. An anti-tumor agent comprising as the active ingredient a platinum complex represented by the following formula I or a steric isomer thereof:

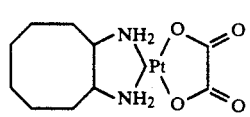
3. A method of curing tumors, which comprises using a platinum complex represented by the following formula I or a steric isomer thereof:
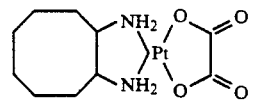
* * * * *